United States Patent [19]

Prospero et al.

[11] Patent Number: 5,520,351

[45] Date of Patent: May 28, 1996

[54] HEATED THREAD TENSIONER ASSEMBLY

[75] Inventors: Richard M. Prospero, Princeton; Erik Lunde, Morganville; Harry Swanson, Bloomfield; Lee Adams, Flemington, all of N.J.

[73] Assignee: Johnson & Johnson Consumer Products, Inc., Skillman, N.J.

[21] Appl. No.: 381,511

[22] Filed: Jan. 31, 1995

[51] Int. Cl.$^6$ ............................. B65H 23/16; B65H 59/10
[52] U.S. Cl. ...................... 242/419.7; 66/146; 242/153; 242/154
[58] Field of Search ................ 242/419.7, 154, 242/153; 66/125 A, 146

[56] References Cited

U.S. PATENT DOCUMENTS

| | | | |
|---|---|---|---|
| 1,508,503 | 9/1924 | Brown et al. | 242/153 |
| 2,082,443 | 6/1937 | Desjardins | 242/153 |
| 2,209,398 | 7/1940 | Garrett | 242/153 |
| 3,191,885 | 6/1965 | Jones et al. | 242/154 |
| 3,297,264 | 1/1967 | Gilbos | 242/150 R |
| 3,449,898 | 6/1969 | Fujita et al. | 57/34 |
| 3,485,429 | 12/1969 | Hutzenlaub | 226/97 |
| 3,559,916 | 2/1971 | Hilscher | 242/153 |
| 3,582,021 | 6/1971 | Cocker | 242/154 |
| 3,590,568 | 11/1969 | Kubevy | 57/35 |
| 3,802,382 | 4/1974 | Koller | 118/78 |
| 3,890,924 | 6/1975 | Horstmann | 118/78 |
| 4,029,113 | 6/1977 | Guyton | 132/91 |
| 4,046,102 | 9/1977 | Piro | 118/78 |
| 4,165,603 | 8/1979 | Lattion | 57/296 |
| 4,193,372 | 3/1980 | Eckholt | 118/713 |
| 4,194,350 | 3/1980 | Schellenberg et al. | 57/352 |
| 4,244,176 | 1/1981 | Shimizu et al. | 57/295 |
| 4,345,542 | 8/1982 | Hauner | 118/78 |
| 4,501,221 | 2/1985 | Landwehrkamp et al. | 118/78 |
| 4,731,217 | 3/1988 | Gerhartz et al. | 264/555 |
| 5,226,435 | 7/1993 | Suhonen et al. | 132/321 |
| 5,284,169 | 2/1994 | Gilligan et al. | 132/321 |

Primary Examiner—William Stryjewski

[57] ABSTRACT

A method and apparatus for maintaining a moving string of waxed thread at a tension. A tensioner mounting frame has a thread input opening for receiving waxed thread from a thread supply, and a thread output opening for outputting the string of waxed thread at a preset tension. A tensioner arm with a plurality of eyelets affixed thereto is provided for guiding the string of waxed thread. The tensioner arm is pivotally connected to the tensioner mounting frame. A plurality of tensioner rods are also provided for guiding the string of waxed thread, the plurality of tensioner rods are rigidly affixed to the tensioner mounting frame. A spring, having a first end coupled to the tensioner mounting frame and a second end coupled to the tensioner arm, creates a tension in the string of waxed thread. A heating device is affixed to the tensioner mounting frame and is provided for warming the apparatus during its operation.

8 Claims, 2 Drawing Sheets

HEATED THREAD TENSIONER ASSEMBLY

FIELD OF THE INVENTION

The present invention relates generally to systems for processing waxed threads or yarns. More particularly, the present invention relates to systems used in winding waxed threads or yarns. Still more particularly, the present invention relates to systems for creating and maintaining tension in a moving string of waxed dental floss during the winding of such dental floss onto a winding core.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

Dental floss is typically distributed in dispensers that have circular bobbins rotatably mounted therein. Each bobbin is formed of a core that has been wound with dental floss. The tail end of floss from the bobbin is typically threaded first through an eyelet at the top of the dispenser and then through a cut bar that is also positioned at the top of the dispenser. In order to draw a length of floss from the dispenser, a user grasps the tail end of the floss, pulls until the desired length of floss has been drawn from the dispenser, and then cuts the drawn length using the cut bar. As the user pulls the floss from the dispenser, the bobbin in the dispenser rotates, thereby allowing the floss on the bobbin to unwind.

During the manufacturing of dental floss products, automated winding machines are used to wind floss onto empty bobbin cores. These winding machines often function at a high speed and may wind many yards of dental floss each minute. In order for the floss to wind properly onto the empty bobbin cores during the winding process, it is important that the tension of the floss be maintained at a preset level as the floss is wound onto the bobbin cores. Devices for creating tension in strings of moving thread are known in the art. One example of such a tensioner device is manufactured by the Steel Heddle Company.

As mentioned above, during the winding of waxed dental flosses, the waxed floss must pass through a tensioner device at a high rate of speed. However, it was found that the forces exerted on the waxed floss as it passed through known tensioner devices caused wax to be separated from the floss and deposited onto the workings of the tensioner device. The wax build-up on the tensioner device from the floss resulted in frequent malfunctioning of the tensioner device. In addition, the waxed thread exiting the tensioner device was not fully satisfactory, because a portion of the wax that was originally on the floss was stripped by the tensioner device.

It is therefore an object of the present invention to provide an efficient system for maintaining tension in waxed threads or yarns during the winding of such threads and yarns.

It is a further objection of the present invention to provide a system for reducing or eliminating the building-up of wax on tensioner devices used during the winding of waxed threads or yarns.

It is a still further objection of the present invention to provide a system for reducing or eliminating the unwanted stripping of wax from waxed threads or yarns by tensioner devices used during the winding of such waxed threads or yarns.

These and still other objects of the invention will become apparent upon study of the accompanying drawings and description of the invention.

SUMMARY OF THE INVENTION

The present invention is directed to a method and apparatus for maintaining a moving string of waxed thread at a tension. A tensioner mounting frame has a thread input opening for receiving waxed thread from a thread supply, and a thread output opening for outputting the string of waxed thread at a preset tension. A tensioner arm with a plurality of eyelets affixed thereto is provided for guiding the string of waxed thread. The tensioner arm is pivotally connected to the tensioner mounting frame. A plurality of tensioner rods are also provided for guiding the string of waxed thread. The plurality of tensioner rods are rigidly affixed to the tensioner mounting frame. A spring, having a first end coupled to the tensioner mounting frame and a second end coupled to the tensioner arm, creates a tension in the string of waxed thread. A heating means is affixed to the tensioner mounting frame and is provided for warming the apparatus during its operation.

DETAILED DESCRIPTION OF THE PREFERRED EMBODIMENT

Figure 1:
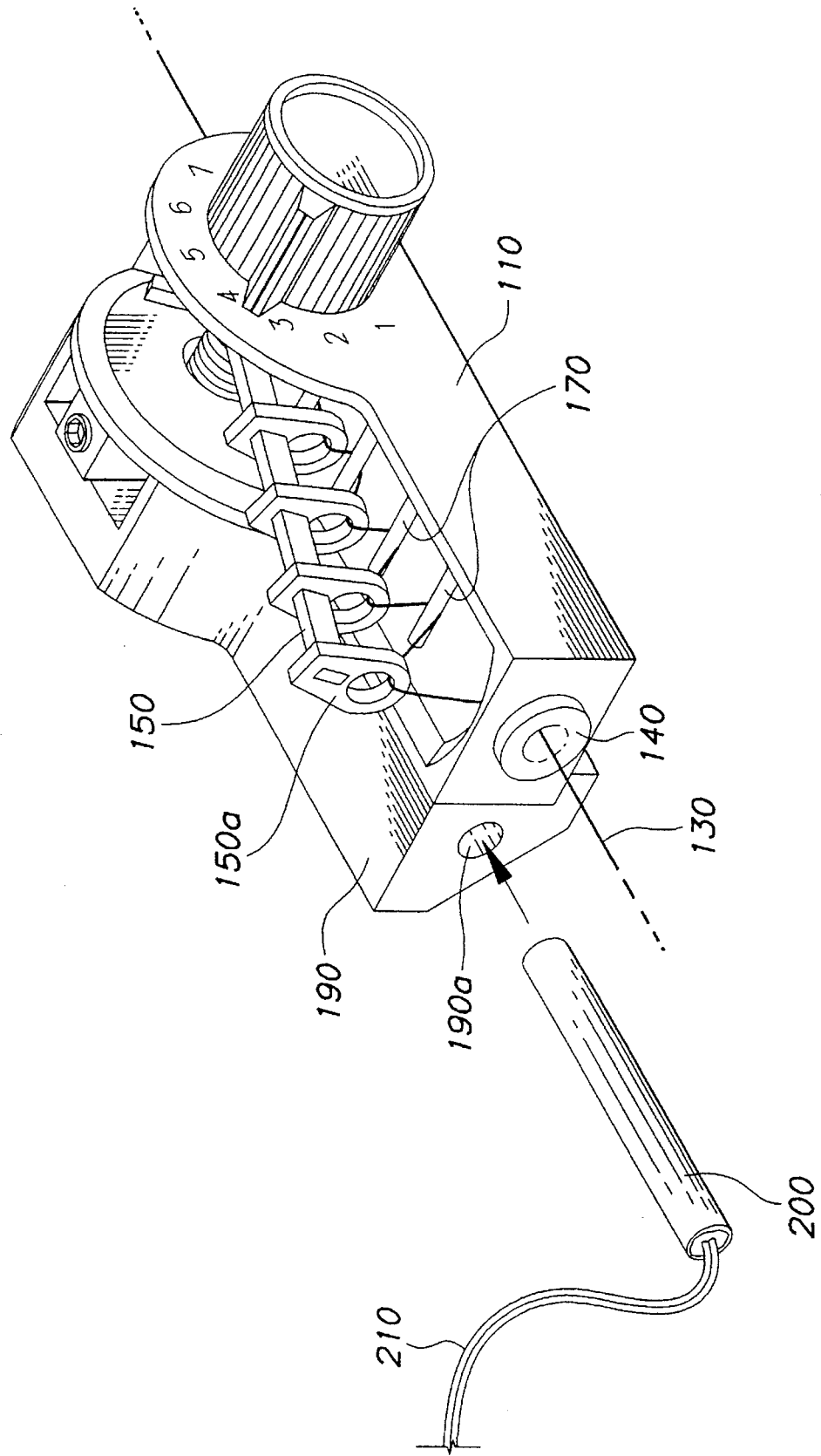
FIG. 1 shows a perspective view of a heated tensioner assembly in accordance with a preferred embodiment the present invention.
Figure 2:
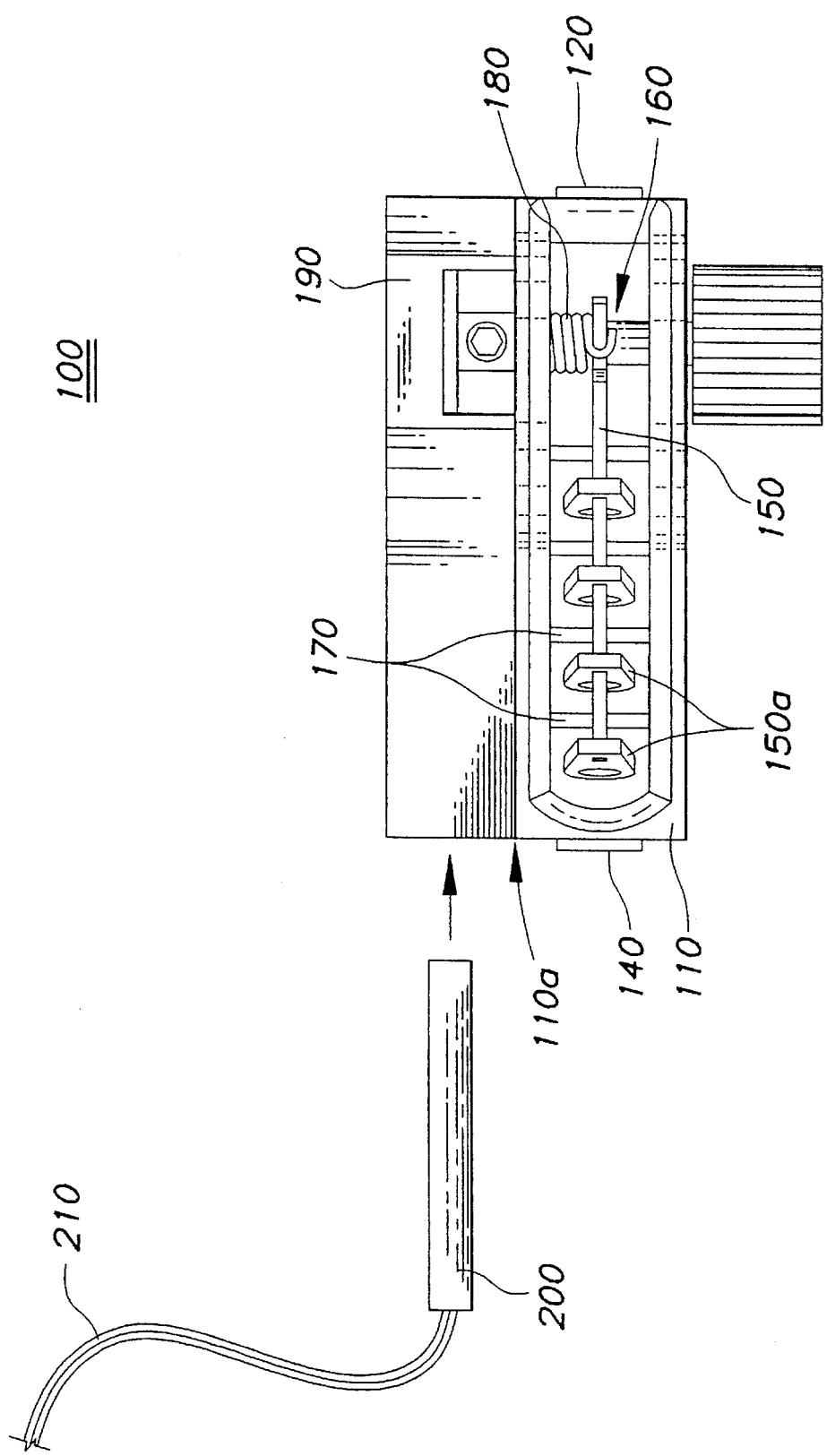
FIG. 2 shows a top view of a heated tensioner assembly in accordance with a preferred embodiment of the present invention.

Referring now to FIGS. 1 and 2, there are shown perspective and top views, respectively, of a heated tensioner assembly 100 in accordance with a preferred embodiment of the present invention. Tensioner assembly 100 includes a tensioner mounting frame 110 having a thread input opening 120 for receiving waxed thread or yarn 130 from a thread supply area (not shown). Waxed thread or yarn 130 may, for example, be formed from a waxed dental floss. Tensioner mounting frame 110 also includes a thread output opening 140 for outputting the string of waxed thread 130 from tensioner assembly 100 at a preset tension.

A tensioner arm 150 is provided with a plurality of eyelets 150*a* affixed thereto for guiding the string of waxed thread 130 through tensioner assembly 100. The tensioner arm 150 is pivotally connected to the tensioner mounting frame 110 at pivot point 160. A plurality tensioner rods 170 are also provided for guiding the string of waxed thread 130 through tensioner assembly 100. Tensioner rods 170 are rigidly affixed to the tensioner mounting frame 110. An adjustable spring 180, having a first end coupled to the tensioner mounting frame 110 and a second end coupled to the tensioner arm 150, creates a tension in the portion of string 130 exiting output opening 140.

A heat distribution block 190 is affixed to the tensioner mounting frame 110 and is provided for transferring heat from heating rod 200 to the tensioner assembler 100 during operation of tensioner assembly 100. In the preferred embodiment, the tensioner mounting frame 110 has a flat rear surface 110a, and heat distribution block 190 has a mating surface corresponding in shape to the flat rear surface. Thus, in the preferred embodiment, heat distribution block 190 extends along the entire length and width of the rear surface 110a of tensioner mounting frame 110. Heater rod 200 is preferably positioned within the heat distribution block 190 at opening 190a. Heater rod 200 is preferably a resistive heating element that generates heat as current is supplied to the rod through power cord 210.

In the preferred embodiment, heater rod 200 is powered continuously at the rate of approximately 10 watts during the operation of tensioner assembly 100. It was found that the continuous flow of approximately 10 watts of power to rod 200 was sufficient to maintain heat distribution block 190 at a temperature slightly exceeding the melting point of any wax (such as microcrystaline wax) that is typically used to form waxed flosses. It will be understood by those skilled in the art that a temperature feedback control system could alternatively be used to maintain heating distribution block 190 at a constant temperature. It will also be understood by those skilled in the art that other configurations and heating devices, such as, for example, hot air heaters or high intensity lighting could also be used to warm tensioner assembly 100 during its operation.

It was found that when tensioner assembly 100 was heated by heat distribution block 190 and heater rod 200 as described above, little or no wax from thread 130 built-up on tensioner assembly 100 during operation of the device, and little or no wax was stripped from thread 130 as it passed through tensioner assembly 100. In contrast to prior unheated tensioner assemblies which typically required stoppage every 30 minutes for wax removal in order to avoid malfunctioning, the heated tensioner assembly of the present invention is able to run continuously without any interruption for wax removal.

Although the preferred embodiment of the present invention is described in connection with a waxed dental floss, it will be understood by those skilled in the art that the present invention may be used in conjunction with any other types of waxed threads or yarns.

The present invention may be embodied in other specific forms without departing from the spirit or essential attributes of the invention. Accordingly, reference should be made to the appended claims, rather than the foregoing specification, as indicating the scope of the invention.

What is claimed is:

1. An apparatus for maintaining a moving string of waxed thread at a tension, comprising:

(A) a tensioner mounting frame having a thread input opening for receiving said waxed thread from a thread supply, and a thread output opening for outputting said string of waxed thread at said tension;

(B) a tensioner arm with a plurality of eyelets affixed thereto for guiding said string of waxed thread, said tensioner arm being pivotally connected to said tensioner mounting frame;

(C) a plurality of tensioner rods for guiding said string of waxed thread, said plurality of tensioner rods being rigidly affixed to said tensioner mounting frame;

(D) a spring, having a first end coupled to said tensioner mounting frame and a second end coupled to said tensioner arm, for creating a tension in said string of waxed thread;

(E) heating means, affixed to said tensioner mounting frame, for warming said apparatus.

2. The apparatus of claim 1, wherein said tensioner mounting frame has a flat rear surface, and said heating means includes a heat distribution block having a mating surface corresponding in shape to said flat rear surface.

3. The apparatus of claim 2, wherein said heating means further includes a heater rod positioned within said heat distribution block.

4. The apparatus of claim 3, wherein said waxed thread is a waxed dental floss formed from a wax, and said heating means is adapted to warm said apparatus above a melting temperature of said wax.

5. A method for maintaining a moving string of waxed thread at a tension, comprising the steps of:

(A) receiving said waxed thread into a tensioner assembly at a thread input opening;

(B) passing said string of waxed thread through said tensioner assembly, said tensioner assembly including a tensioner mounting frame having a thread output opening for outputting said string of waxed thread at said tension, a tensioner arm with a plurality of eyelets affixed thereto for guiding said string of waxed thread, said tensioner arm being pivotally connected to said tensioner mounting frame, a plurality of tensioner rods for guiding said string of waxed thread, said plurality of tensioner rods being rigidly affixed to said tensioner mounting frame, and a spring, having a first end coupled to said tensioner mounting frame and a second end coupled to said tensioner arm, for creating a tension in said string of waxed thread; and (C) heating said tensioner assembly with a heating means while performing steps (A) and (B).

6. The method of claim 5, wherein said tensioner mounting frame has a flat rear surface, and said heating means includes a heat distribution block having a mating surface corresponding in shape to said flat rear surface.

7. The method of claim 6, wherein said heating means further includes a heater rod positioned within said heat distribution block.

8. The method of claim 7, wherein said waxed thread is a waxed dental floss formed from a wax, and said heating step includes heating said tensioner assembly above a melting temperature of said wax.

* * * * *